United States Patent
Kurzke et al.

(10) Patent No.: US 9,968,251 B2
(45) Date of Patent: May 15, 2018

(54) COMBINED STRUCTURE-FUNCTION GUIDED PROGRESSION ANALYSIS

(71) Applicant: Carl Zeiss Meditec, Inc., Dublin, CA (US)

(72) Inventors: Tobias Kurzke, Pleasanton, CA (US); Matthias Monhart, Winterthur (CH); Vincent Michael Patella, Albany, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 50 days.

(21) Appl. No.: 15/281,497

(22) Filed: Sep. 30, 2016

(65) Prior Publication Data

US 2018/0092526 A1  Apr. 5, 2018

(51) Int. Cl.
*A61B 3/00* (2006.01)
*A61B 3/10* (2006.01)
(Continued)

(52) U.S. Cl.
CPC .......... *A61B 3/0058* (2013.01); *A61B 3/0025* (2013.01); *A61B 3/024* (2013.01);
(Continued)

(58) Field of Classification Search
CPC ........... A61B 3/14; A61B 3/102; A61B 3/103; A61B 3/113
(Continued)

(56) References Cited

U.S. PATENT DOCUMENTS

| 5,381,195 A | 1/1995 | Rootzen et al. |
| 5,461,435 A | 10/1995 | Rootzen et al. |

(Continued)

FOREIGN PATENT DOCUMENTS

| EP | 1666009 A2 | 6/2006 |
| JP | 9-313447 A | 12/1997 |

(Continued)

OTHER PUBLICATIONS

Advisory Action received for U.S. Appl. No. 12/849,686, dated Jan. 3, 2014, 3 pages.
(Continued)

*Primary Examiner* — Jack Dinh
(74) *Attorney, Agent, or Firm* — Morrison & Foerster LLP (57) ABSTRACT

Various methods of displaying combined structural and functional disease progression information of a patient's eye are described. In one exemplary method, a set of structural measurements of the patient's eye is received. The set of structural measurements are taken at a plurality of testing dates. A set of functional measurements of the patient's eye is received. The set of functional measurements are taken at a plurality of testing dates. A single viewport comprising a side by side display of structural and functional measurements over a common time scale is generated, which is then displayed or the results of the generated viewport are stored. The structural and functional measurements are arranged in a chronological order of testing dates over the common time scale. Further, a structural and a functional measurement that have testing dates falling within a certain time period are placed in close proximity to each other for comparison purposes.

30 Claims, 7 Drawing Sheets

(51) Int. Cl.
*A61B 5/00* (2006.01)
*A61B 3/024* (2006.01)

(52) U.S. Cl.
CPC ............ *A61B 3/102* (2013.01); *A61B 3/1005* (2013.01); *A61B 5/4842* (2013.01)

(58) Field of Classification Search
USPC ................................................ 351/200–246
See application file for complete search history.

(56) References Cited

U.S. PATENT DOCUMENTS

| | | | |
|---|---|---|---|
| 5,598,235 | A | 1/1997 | Heijl et al. |
| 5,878,746 | A | 3/1999 | Lemelson et al. |
| 6,068,377 | A | 5/2000 | McKinnon et al. |
| 6,247,812 | B1 | 6/2001 | Miehle et al. |
| 6,293,674 | B1 | 9/2001 | Huang et al. |
| 6,735,331 | B1 | 5/2004 | Binnun et al. |
| 7,166,079 | B2 | 1/2007 | Febbroriello et al. |
| 7,237,898 | B1 | 7/2007 | Hohla et al. |
| 7,306,560 | B2 | 12/2007 | Iliff |
| 7,392,199 | B2 | 6/2008 | Karlov et al. |
| 7,406,200 | B1 | 7/2008 | Syeda-Mahmood et al. |
| 7,458,936 | B2 | 12/2008 | Zhou et al. |
| 7,519,227 | B1 | 4/2009 | Syeda-Mahmood et al. |
| 8,132,916 | B2 | 3/2012 | Johansson |
| 9,332,902 | B2 | 5/2016 | Tumlinson et al. |
| 9,357,911 | B2 | 6/2016 | Bizios et al. |
| 2004/0105073 | A1 | 6/2004 | Maddalena et al. |
| 2005/0094099 | A1 | 5/2005 | Newman et al. |
| 2006/0025658 | A1 | 2/2006 | Newman et al. |
| 2006/0084856 | A1 | 4/2006 | Biggins et al. |
| 2006/0114411 | A1 | 6/2006 | Wei et al. |
| 2007/0038042 | A1 | 2/2007 | Freeman et al. |
| 2007/0197932 | A1 | 8/2007 | Feke et al. |
| 2008/0309881 | A1 | 12/2008 | Huang et al. |
| 2008/0312552 | A1 | 12/2008 | Zhou et al. |
| 2009/0073387 | A1 | 3/2009 | Meyer et al. |
| 2009/0119021 | A1 | 5/2009 | Schuett et al. |
| 2009/0244485 | A1 | 10/2009 | Walsh et al. |
| 2010/0238405 | A1 | 9/2010 | Newman et al. |
| 2010/0241450 | A1 | 9/2010 | Gierhart et al. |
| 2010/0249532 | A1 | 9/2010 | Maddess et al. |
| 2010/0277691 | A1 | 11/2010 | Huang et al. |
| 2010/0290005 | A1 | 11/2010 | Huang et al. |
| 2010/0290006 | A1 | 11/2010 | Flanagan et al. |
| 2011/0046480 | A1 | 2/2011 | Yonezawa |
| 2011/0190657 | A1 | 8/2011 | Zhou et al. |
| 2012/0287401 | A1 | 11/2012 | Bizios et al. |
| 2013/0181976 | A1 | 7/2013 | Dastmalchi et al. |

FOREIGN PATENT DOCUMENTS

| | | | |
|---|---|---|---|
| JP | 2005-301816 | A | 10/2005 |
| JP | 2008-73188 | A | 4/2008 |
| WO | 2007/098070 | A2 | 8/2007 |
| WO | 2007/098070 | A3 | 6/2008 |

OTHER PUBLICATIONS

Advisory Action received for U.S. Appl. No. 13/467,907, dated Apr. 23, 2015, 3 pages.
Advisory Action Received for U.S. Appl. No. 13/467,907, dated May 1, 2014, 4 pages.
Agarwal et al., "Target Intraocular Pressure in Glaucoma Management", Asian Journal of Ophthalmology, vol. 3, No. 3,4, 2001, pp. 15-18.
Ajtony et al., "Relationship between Visual Field Sensitivity and Retinal Nerve Fiber Layer Thickness as Measured by Optical Coherence Tomography", Investigative Ophthalmology & Visual Science, vol. 48, No. 1, Jan. 2007, pp. 258-263.
Anderson et al., "Encounters in Glaucoma Research 3", Kugler Publications BV, 1996, pp. 184-186.
Artes et al., "Longitudinal Changes in the Visual Field and Optic Disc in Glaucoma", Progress in Retinal and Eye Research, vol. 24, 2005, pp. 333-354.
Arthur et al., "Agreement in Assessing Cup-to-Disc Ratio Measurement among Stereoscopic Optic Nerve Head Photographs, HRT II, and Stratus OCT", Journal of Glaucoma, vol. 15, No. 3, Jun. 2006, pp. 183-189.
Asman et al., "Glaucoma Hemifield Test: Automated Visual Field Evaluation", Archives of Ophthalmology, vol. 110, Jun. 1992, pp. 812-819.
Bengtsson et al., "A New Generation of Algorithms for Computerized Threshold Perimetry, SITA", Acta Ophthalmologica Scandinavica, vol. 75, 1997, pp. 368-375.
Bengtsson et al., "A Visual Field Index for Calculation of Glaucoma Rate of Progression", American Journal of Ophthalmology, vol. 145, No. 2, Feb. 2008, pp. 343-353.
Bengtsson et al., "Effects of Input Data on the Performance of a Neural Network in Distinguishing Normal and Glaucomatous Visual Field", Investigative Ophthalmology & Visual Science, vol. 46, No. 10, Oct. 2005, pp. 3730-3736.
Bizios et al., "Integration and Fusion of Standard Automated Perimetry and Optical Coherence Tomography Data for Improved Automated Glaucoma Diagnostics", BMC Ophthalmology, vol. 11, No. 20, 2011, pp. 1-11.
Bizios et al., "Machine Learning Classifiers for Glaucoma Diagnosis based on Classification of Retinal Nerve Fibre Layer Thickness Parameters Measured by Stratus OCT", Acta Ophthalmologica, vol. 88, 2010, pp. 44-52.
Bizios et al., "Trained Artificial Neural Network for Glaucoma Diagnosis Using Visual Field Data: A Comparison With Conventional Algorithms", Journal of Glaucoma, vol. 16, No. 11 2007, pp. 20-28.
Blazkiewicz et al., "Signal-to-Noise Ratio Study of Full-Field Fourier-Domain Optical Coherence Tomography", Applied Optics, vol. 44, No. 36, Dec. 20, 2005, pp. 7722-7729.
Boland et al., "Evaluation of a Combined Index of Optic Nerve Structure and Function for Glaucoma Diagnosis", Boland and Quigley BMC Ophthalmology, vol. 11, No. 6, 2011, pp. 1-12.
Bowd et al., "Bayesian Machine Learning Classifiers for Combining Structural and Functional Measurements to Classify Healthy and Glaucomatous Eyes", Investigative Ophthalmology & Visual Science, vol. 49, No. 3, Mar. 2008, pp. 945-953.
Bowd et al., "Comparing Neural Networks and Linear Discriminant Functions for Glaucoma Detection using Confocal Scanning Laser Ophthalmoscopy of the Optic Disc", Investigative Ophthalmology & Visual Science , vol. 43, No. 11, Nov. 2002, pp. 3444-3454.
Bowd et al., "Machine Learning Classifiers in Glaucoma", Optometry and Vision Science, vol. 85, No. 6, Jun. 2008, pp. 396-405.
Brusini et al., "Staging Functional Damage in Glaucoma: Review of different Classification Methods", Survey of Ophthalmology, vol. 52, No. 2, Mar.-Apr. 2007, pp. 156-179.
Budenz et al., "Reproducibility of Retinal Nerve Fiber Thickness Measurements Using the Stratus OCT in Normal and Glaucomatous Eyes", Investigative Ophthalmology & Visual Science, vol. 46, No. 7, Jul. 2005, pp. 2440-2443.
Budenz et al., "Sensitivity and Specificity of the StratusOCT for Perimetric Glaucoma", Ophthalmology, vol. 112, No. 1, Jan. 2005, pp. 3-9.
Burgansky-Eliash et al., "Optical Coherence Tomography Machine Learning Classifiers for Glaucoma Detection: A Preliminary Study", Investigative Ophthalmology & Visual Science, vol. 46, No. 11, Nov. 2005, pp. 4147-4152.
Chan et al., "Comparison of Machine Learning and Traditional Classifiers in Glaucoma Diagnosis", IEEE Transactions on Biomedical Engineering, vol. 49, No. 9, Sep. 2002, pp. 963-974.
Chang et al., "New Developments in Optical Coherence Tomography for Glaucoma", Current Opinion in Ophthalmology, vol. 19, 2008, pp. 127-135.
Chauhan et al., "Optic Disc and Visual Field Changes in a Prospective Longitudinal Study of Patients With Glaucoma: Comparison of Scanning Laser Tomography With Conventional Perimetry and Optic Disc Photography", Arch Ophthalmology, vol. 119, 2001, pp. 1492-1499.

(56) References Cited

OTHER PUBLICATIONS

Chauhan et al., "Technique for Detecting Serial Topographic Changes in the Optic Disc and Peripapillary Retina Using Scanning Laser Tomography", Investigative Ophthalmology & Visual Science, vol. 41, No. 3, Mar. 2000, pp. 775-782.
Chauhan, Balwantray C., "Detection of Glaucomatous Changes in the Optic Disc", Heidelberg Engineering, On-line publication, Dec. 2005, pp. 53-65.
Choma et al., "Sensitivity Advantage of Swept Source and Fourier Domain Optical Coherence Tomography", Optics Express, vol. 11, No. 18, Sep. 8, 2003, pp. 2183-2189.
Danesh-Meyer et al., "Relationship between Retinal Nerve Fiber Layer and Visual Field Sensitivity as Measured by Optical Coherence Tomography in Chiasmal Compression", Investigative Ophthalmology & Visual Science, vol. 47, No. 11, Nov. 2006, pp. 4827-4835.
Delgado et al., "Automated Perimetry: A Report by the American Academy of Ophthalmology", Ophthalmology, vol. 109, No. 12, Dec. 2002, pp. 2362-2374.
Delong et al., "Comparing the Areas under Two or More Correlated Receiver Operating Characteristic Curves: A Nonparametric Approach", Biometrics, vol. 44, No. 3, Sep. 1988, pp. 837-845.
El Beltagi et al., "Retinal Nerve Fiber Layer Thickness Measured with Optical Coherence Tomography is related to Visual Function in Glaucomatous Eyes", Ophthalmology, vol. 110, No. 11, Nov. 2003, pp. 2185-2191.
Ferreras et al., "Mapping Standard Automated Perimetry to the Peripapillary Retinal Nerve Fiber Layer in Glaucoma", Investigative Ophthalmology & Visual Science, vol. 49, No. 7, Jul. 2008, pp. 3018-3025.
Final Office Action received for U.S. Appl. No. 12/157,850, dated Sep. 23, 2013, 15 pages.
Final Office Action received for U.S. Appl. No. 12/849,686, dated Oct. 11, 2013, 12 pages.
Final Office Action received for U.S. Appl. No. 13/467,907, dated Feb. 11, 2014, 18 pages.
Final Office Action received for U.S. Appl. No. 12/157,850 dated Oct. 12, 2012, 13 pages.
Final Office Action received for U.S. Appl. No. 13/467,907, dated Jan. 15, 2015, 14 pages.
Fortune et al., "Retinal Nerve Fiber Layer Birefringence Declines Prior to Thickness After Onset of Experimental Glaucoma or Optic Nerve Transection in Non-Human Primates", Investigative Ophthalmology & Visual Science, Suppl., 49, abstract No. 3761, 2008, 1 page.
Gardiner et al., "Evaluation of the Structure-Function Relationship in Glaucoma", Investigative Ophthalmology & Visual Science, vol. 46, No. 10, Oct. 2005, pp. 3712-3717.
Garway-Heath et al., "Mapping the Visual Field to the Optic Disc in Normal Tension Glaucoma Eyes", American Academy of Ophthalmology, vol. 107, No. 10, Oct. 2000, pp. 1809-1815.
Goldbaum et al., "Comparing Machine Learning Classifiers for Diagnosing Glaucoma from Standard Automated Perimetry", Investigative Ophthalmology & Visual Science, vol. 43, No. 1, Jan. 2002, pp. 162-169.
Goldbaum et al., "Interpretation of Automated Perimetry for Glaucoma by Neural Network", Investigative Ophthalmology & Visual Science, vol. 35, No. 9, Aug. 1994, pp. 3362-3373.
Gotzinger et al., "Retinal Nerve Fiber Layer Birefringence of Healthy and Glaucomatous Eyes Measured with Polarization Sensitive Spectral Domain OCT", Investigative Ophthalmology & Visual Science, Suppl., 49, abstract No. 3762, 2008, 1 page.
Harwerth et al., "Linking Structure and Function in Glaucoma", Progress in Retinal and Eye Research, 2010, pp. 1-23.
Harwerth et al., "Neural Losses Correlated with Visual Losses in Clinical Perimetry", Investigative Ophthalmology & Visual Science, vol. 45, No. 9, Sep. 2004, pp. 3152-3160.
Harwerth et al., "The Relationship between Nerve Fiber Layer and Perimetry Measurements", Investigative Ophthalmology & Visual Science, vol. 48, No. 2, Feb. 2007, pp. 763-773.
Harwerth et al., "Visual Field Defects and Retinal Ganglion Cell Losses in Patients With Glaucoma", Arch Ophthalmology, vol. 124, Jun. 2006, pp. 853-859.
Hillmann et al., "Holoscopy-Holographic Optical Coherence Tomography", Optics Letters, vol. 36, No. 13, Jul. 1, 2011, pp. 2390-2392.
Hood et al., "A Framework for Comparing Structural and Functional Measures of Glaucomatous Damage", Progress in Retinal and Eye Research, vol. 26, 2007, pp. 688-710.
Horn et al., "Continuing Medical Education: Frequency Doubling Technique Perimetry and Spectral Domain Optical Coherence Tomography in Patients with Early Glaucoma", Eye, vol. 25, 2011, pp. 17-29.
Horn et al., "Correlation Between Local Glaucomatous Visual Field Defects and Loss of the Nerve Fiber Layer Thickness Measured with Polarimetry (GDx) and Spectral Domain OCT", Investigative Ophthalmology & Visual Science, Suppl., 49, abstract No. 732, 2008, 1 page.
Hougaard et al., "Glaucoma Detection by Stratus OCT", Journal of Glaucoma, vol. 16, No. 3, May 2007, pp. 302-306.
Hougaard et al., "Modeling the Normal Retinal Nerve Fiber Layer Thickness as Measured by Stratus Optical Coherence Tomography", Graefe's Arch Clin Exp Ophthalmol, vol. 244, 2006, pp. 1607-1614.
Huang et al., "Development and Comparison of Automated Classifiers for Glaucoma Diagnosis Using Stratus Optical Coherence Tomography", Investigative Ophthalmology & Visual Science, vol. 46, No. 11, Nov. 2005, pp. 4121-4129.
Huang et al., "Microtubules Contribute to the Birefringence of the Retinal Nerve Fiber Layer", Investigative Ophthalmology & Visual Science, vol. 46, No. 12, Dec. 2005, pp. 4588-4593.
"Humphrey® Glaucoma Progression Analysis (GPA) Software", Carl Zeiss Meditec, Inc., 2003, 8 pages.
International Preliminary Report on Patentability received for PCT Patent Application No. PCT/EP2010/004846, dated Feb. 23, 2012, 12 pages.
International Search Report and Written Opinion received for PCT Patent Application No. PCT/EP2010/004846, dated Mar. 28, 2011, 18 pages.
Invitation to Pay Additional Fees received for PCT Patent Application No. PCT/EP2010/004846, dated Jan. 13, 2011, 6 pages.
Kanamori et al., "Regional Relationship between Retinal Nerve Fiber Layer Thickness and Corresponding Visual Field Sensitivity in Glaucomatous Eyes", Arch Opthalmology, vol. 126, No. 11, Nov. 24, 2008, pp. 1500-1506.
Kerrigan-Baumrind et al., "Number of Ganglion Cells in Glaucoma Eyes Compared with Threshold Visual Field Tests in the Same Persons", Investigative Ophthalmology & Visual Science, vol. 41, No. 3, Mar. 2000, pp. 741-748.
Leitgeb et al., "Ultrahigh Resolution Fourier Domain Optical Coherence Tomography", Optics Express, vol. 12, No. 10, May 17, 2004, pp. 2156-2165.
Leung et al., "Comparative Study of Retinal Nerve Fiber Layer Measurement by StratusOCT and GDx VCC, II: Structure/Function Regression Analysis in Glaucoma", Investigative Ophthalmology & Visual Science, vol. 46, No. 10, Oct. 2005, pp. 3702-3711.
Lin et al., "Optic Nerve Head and Retinal Nerve Fiber Layer Analysis", Ophthalmology, vol. 114, No. 10, Oct. 2007, pp. 1937-1949.
Mardin et al., "Improving Glaucoma Diagnosis by the Combination of Perimetry and HRT Measurements", Journal of Glaucoma, vol. 15, No. 4, Aug. 2006, pp. 299-305.
Medeiros et al., "Comparison of the GDx VCC Scanning Laser Polarimeter, HRT II Confocal Scanning Laser Ophthalmoscope, and Stratus OCT Optical Coherence Tomograph for the Detection of Glaucoma", Arch Ophthalmology, vol. 122, Jun. 2004, pp. 827-837.
Moller, Martin F., "A Scaled Conjugate Gradient Algorithm for Fast Supervised Learning", PB-339, Nov. 13, 1990, pp. 1-21.
Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.
Non-Final Office Action received for U.S. Appl. No. 13/467,907, dated Sep. 6, 2013, 17 pages.

(56) References Cited

OTHER PUBLICATIONS

Non-Final Office Action received for U.S. Appl. No. 12/157,850, dated Dec. 20, 2013, 14 pages.
Non-Final Office Action received for U.S. Appl. No. 12/157,850, dated Mar. 28, 2013, 14 pages.
Non-Final Office Action received for U.S. Appl. No. 12/157,850, dated Sep. 29, 2011, 14 pages.
Non-Final Office Action received for U.S. Appl. No. 12/849,686, dated Mar. 14, 2013, 10 pages.
Non-Final Office Action received for U.S. Appl. No. 12/849,686, dated Apr. 21, 2014, 11 pages.
Non-Final Office Action received for U.S. Appl. No. 13/467,907, dated Jul. 16, 2014, 13 pages.
Non-Final Office Action received for U.S. Appl. No. 13/467,907, dated Jul. 20, 2015, 16 pages.
Notice of Allowance received for U.S. Appl. No. 13/467,907, dated Feb. 10, 2016, 11 pages.
Notice of Allowance received for U.S. Appl. No. 13/467,907, dated Mar. 15, 2016, 8 pages.
Office Action Received for Japanese Patent Application No. 2012-524139, dated Mar. 4, 2014, 8 pages (4 pages of English Translation and 4 pages of Official Copy).
Patel et al., "EEG and MRI Data Fusion for Early Diagnosis of Alzheimer's Disease", 30th Annual International IEEE EMBS Conference, Aug. 20-24, 2008, pp. 1757-1760.
Patterson et al., "A New Statistical Approach for Quantifying Change in Series of Retinal and Optic Nerve Head Topography Images", Investigative Ophthalmology & Visual Science, vol. 46, No. 5, May 2005, pp. 1659-1667.
Paunescu et al., "Reproducibility of Nerve Fiber Thickness, Macular Thickness, and Optic Nerve Head Measurements using StratusOCT", Investigatative Ophthalmology & Visual Science, vol. 45, No. 6, Jun. 2004, pp. 1716-1724.
Poinoosawmy et al., "The Ability of the GDx Nerve Fibre Analyser Neural Network to Diagnose Glaucoma", Graefe's Arch Clin Exp Ophthalmol, vol. 239, 2001, pp. 122-127.
Porter et al., "Three-Dimensional Registration and Fusion of Ultrasound and MRI Using Major Vessels as Fiducial Markers", IEEE Transactions on Medical Imaging, vol. 20, No. 4, Apr. 2001, pp. 354-359.
Quigley et al., "Optic Nerve Damage in Human Glaucoma: III. Quantitative Correlation of Nerve Fiber Loss and Visual Field Defect in Glaucoma, Ischemic Neuropathy, Papilledema, and Toxic Neuropathy", Arch Ophthalmology, vol. 100, Jan. 1982, pp. 135-146.
Quigley et al., "Retinal Ganglion Cell Atrophy Correlated with Automated Perimetry in Human Eyes with Glaucoma", American Journal of Ophthalmology, vol. 107, No. 5, May 1989, pp. 453-464.
Racette et al., "Combining Functional and Structural Tests improves the Diagnostic Accuracy of Relevance Vector Machine Classifiers", Journal of Glaucoma, vol. 19, No. 3, Mar. 2010, pp. 167-175.
Reus et al., "Scanning Laser Polarimetry of the Retinal Nerve Fiber Layer in Perimetrically Unaffected Eyes of Glaucoma Patients", American Academy of Ophthalmology, vol. 111, No. 12, Dec. 2004, pp. 2199-2203.
Reus et al., "The Relationship between Standard Automated Perimetry and GDx VCC Measurements", Investigative Ophthalmology & Visual Science, vol. 45, No. 3, Mar. 2004, pp. 840-845.
Sample et al., "Unsupervised Machine Learning with Independent Component Analysis to Identify Areas of Progression in Glaucomatous Visual Fields", Investigative Ophthalmology & Visual Science, vol. 46, No. 10, Oct. 2005, pp. 3684-3692.
Sato et al., "Correlation between Retinal Nerve Fibre Layer Thickness and Retinal Sensitivity", Acta Ophthalmologica, vol. 86, 2008, pp. 609-613.
Schuman et al., "Reproducibility of Nerve Fiber Layer Thickness Measurements Using Optical Coherence Tomography", Ophthalmology, vol. 103, No. 11, Nov. 1996, pp. 1889-1898.
Shah et al., "Combining Structural and Functional Testing for Detection of Glaucoma", American Academy of Ophthalmology, vol. 113, No. 9, Sep. 2006, pp. 1593-1602.
Sherman et al., "Discordance between Structure and Function in Glaucoma: Possible Anatomical Explanations", Optometry, vol. 80, Sep. 2009, pp. 487-501.
Sommer et al., "Clinically Detectable Nerve Fiber Atrophy Precedes the Onset of Glaucomatous Field Loss", Arch Ophthalmol, vol. 109, Jan. 1991, pp. 77-83.
Strouthidis et al., "Structure and Function in Glaucoma: The Relationship between a Functional Visual Field Map and an Anatomic Retinal Map", Investigative Ophthalmology & Visual Science, vol. 47, No. 12, Dec. 2006, pp. 5356-5362.
Swanson et al., "Perimetric Defects and Ganglion Cell Damage: Interpreting Linear Relations Using a Two-Stage Neural Model", Investigative Ophthalmology & Visual Science, vol. 45, No. 2, Feb. 2004, pp. 466-472.
Tucker et al., "A Spatio-Temporal Bayesian Network Classifier for Understanding Visual Field Deterioration", Artificial Intelligence in Medicine, vol. 34, 2005, pp. 163-177.
Turpin et al., "Combining Ganglion Cell Topology and Data of Patients with Glaucoma to Determine a Structure-Function Map", Investigative Ophthalmology & Visual Science, vol. 50, No. 7, Jul. 2009, pp. 3249-3256.
Vermeer et al., "Modeling of Scanning Laser Polarimetry Images of the Human Retina for Progression Detection of Glaucoma", IEEE Transactions on Medical Imaging, vol. 25, No. 5, May 2006, pp. 517-528.
Wald, Lucien, "Some Terms of Reference in Data Fusion", IEEE Transactions on Geoscience and Remote Sensing, vol. 37, No. 3, May 1999, pp. 1190-1193.
Zhou et al., "Progress Analysis Algorithms for GDx VCC Retinal Nerve Fiber Layer Measurements", Arvo Abstract, 2006, 1 page.
Zhu et al., "Combining Structural and Functional Measurements to Improve Reproducibility of Follow Up Data in Glaucoma", Investigative Ophthalmology & Visual Science, abstract No. 2572, 2009, 4 pages.
Zhu et al., "Predicting Visual Function from the Measurements of Retinal Nerve Fiber Layer Structure", Investigative Ophthalmology & Visual Science, vol. 51, No. 11, Nov. 2010, pp. 5657-5666.

COMBINED STRUCTURE-FUNCTION GUIDED PROGRESSION ANALYSIS

FIELD OF THE INVENTION

This invention generally relates to the field of displaying combined structural and functional progression information to a user. In particular, the invention discloses various methods of displaying optical coherence tomography (OCT) and visual field exam information together on the same screen or viewport, so that their respective progression can easily be compared to each other and assessed.

BACKGROUND

Glaucoma is a major eye disease that arises from progressive damage to the optic nerve (ON) and retinal ganglion cells (RGCs) and their axons, the retinal nerve fiber layer (RNFL). If left untreated, it can lead to permanent nerve damage and blindness. Therefore, determining the rate of progression in glaucomatous patients is crucial in glaucoma management.

Progression can be detected using structural measurements (e.g., OCT measurements of the retinal nerve fiber layer (RNFL) and ganglion cell layer), or functional measurements (e.g., visual field exams), or both. Often times, but not always, progression can be observed by an OCT measurement, before the visual field is impacted. However, at later disease stages, no further RNFL thinning can be observed based on the OCT measurement ('OCT floor effect') and a visual field measurement may become the only metric to determine the change or progression.

The Cirrus HD-OCT™ (Carl Zeiss Meditec, Inc. Dublin, Calif.) is one type of commercially available spectral domain OCT (SD-OCT) system that can be used to provide structural measurements. The Humphrey HFA (Carl Zeiss Meditec, Inc. Dublin, Calif.) is one type of standard automated perimeter that can be used to provide functional measurements. Guided progression analysis has been available for both the Cirrus HD-OCT and HFA, however the analysis is currently separated by instrument type, and is only accessible independently from each other. No integrated view including both the structural and functional measurements on progression information from different systems is available, thus interpreting this data on separate systems is difficult and time consuming.

Therefore, there is a need for a method or technique that can display results of both the structural and functional measurements on a single screen or point of contact in an efficient way, so that their respective progressions can easily be compared to each other and assessed.

SUMMARY

According to one aspect of the subject matter described in the present application, a method of displaying combined structural and functional disease progression information of a patient's eye includes receiving a set of structural measurements of the patient's eye, said set of structural measurements taken at a plurality of testing dates; receiving a set of functional measurements of the patient's eye, said set of functional measurements taken at a plurality of testing dates; generating a single viewport comprising a side by side display of structural and functional measurements over a common time scale, wherein each of the structural and functional measurements in the generated viewport has a testing date falling within the common time scale; and displaying the generated single viewport or storing results of the generated single viewport. The common time scale can include dates extending beyond the range of dates over which structural or functional data was taken. The two types of data need not be taken on the same dates.

According to another aspect of the subject matter described in the present application, a method of displaying combined structural and functional disease progression information of a patient's eye includes receiving a set of structural measurements of the patient's eye, said set of structural measurements taken at a plurality of testing dates; receiving a set of functional measurements of the patient's eye, said set of functional measurements taken at a plurality of testing dates; computing one or more structural metrics from the set of structural measurements; computing one or more functional metrics from the set of functional measurements; generating a single viewport comprising a side by side display of the one or more structural metrics and the one or more functional metrics, wherein the one or more structural metrics and the one or more functional metrics are each displayed on a common time axis; and displaying the generated single viewport or storing results of the generated single viewport.

According to yet another aspect of the subject matter described in the present application, a method of displaying combined structural and functional disease progression information of a patient's eye includes receiving a set of structural measurements of the patient's eye, said set of structural measurements taken at a plurality of testing dates; receiving a set of functional measurements of the patient's eye, said set of functional measurements taken at a plurality of testing dates; computing one or more structural metrics from the set of structural measurements; computing one or more functional metrics from the set of functional measurements; generating a single viewport comprising 1) a first side by side display of the one or more structural metrics and the one or more functional metrics, wherein the one or more structural metrics and the one or more functional metrics are each displayed on a common time axis, and 2) a second side by side display of structural and functional measurements over a common time scale, wherein each of the structural and functional measurements in the second side by side display has a testing date falling within the common time scale; and displaying the generated single viewport or storing results of the generated single viewport.

The invention discussed herein is particularly advantageous in a number of respects. For instance, the invention enables a user (e.g., a doctor, a clinician) to view all available information time-matched (approximately) at a single point of contact instead of looking at the patient's data separately per instrument type. This allows the user to get a more holistic picture of the patient's condition, taking into account both the functional and structural states, as well as their change over time.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIGS. 3A-3C are flowcharts of example methods of integrating and displaying structural and functional disease progression information of a patient's eye in a single viewport to a user. In particular.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

System Overview
Example Optical Coherence Tomography (OCT) System for Structural Measurements OCT is a non-invasive, in-vivo imaging technique that is based on the back-scatter or reflectivity of light in a medium. OCT is particularly valuable in ophthalmic examinations, where the beam of light produced by the OCT device scans the eye through the pupil and the image formation process records the back-scattering profile of the light at each location. The intensity of the back-scattered light is indicative of the scattering properties of the tissue and tissue boundaries, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice.

Figure 1:
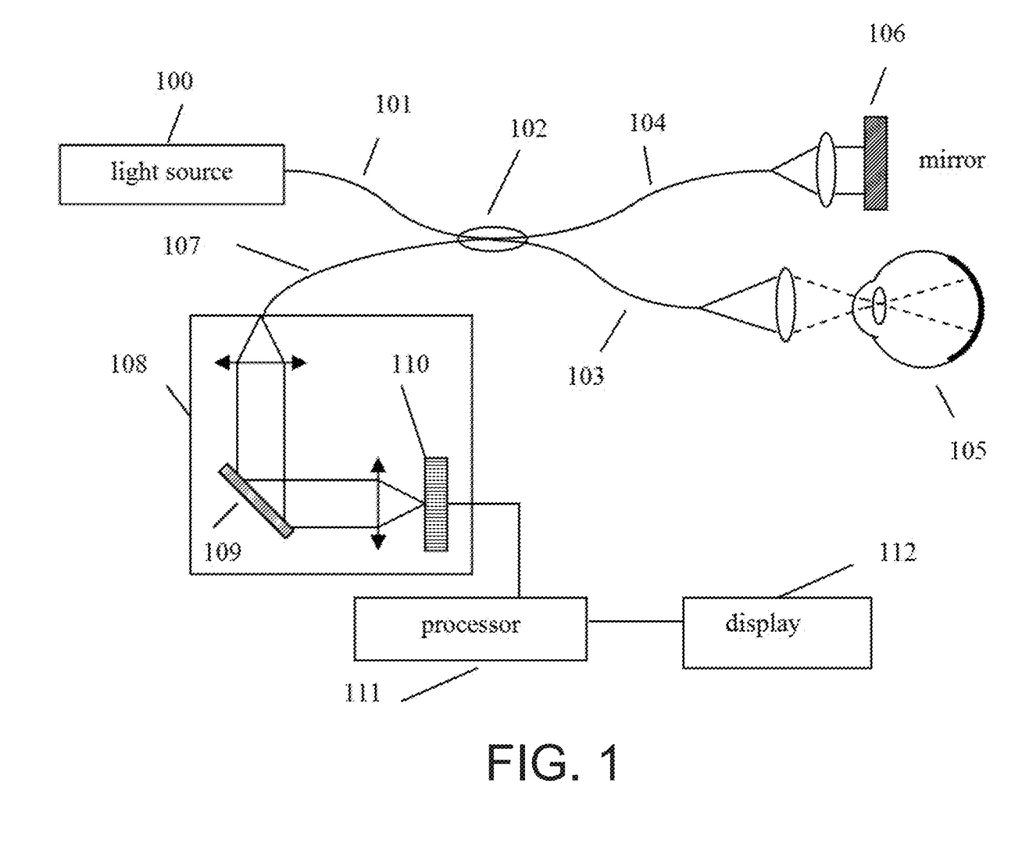
FIG. 1 illustrates one example of an ophthalmic imaging system (specifically, a spectral-domain optical coherence tomography (SD-OCT) system) that can be used to collect structural measurements of a patient's eye for use in the present invention.

Several implementations of OCT have been developed including time domain (TD-OCT) and frequency domain (spectral domain (SD-OCT) and swept-source (SS-OCT)). FIG. 1 shows a basic block diagram for a spectrometer based SD-OCT system that can be used to provide structural measurement data for the present invention. The light source 100 provides broad bandwidth light to a short length of an optical fiber 101 to an input port of a fiber optic coupler 102, which splits the incoming light beam into the two arms of an interferometer. The two arms each have a section of optical fiber 103 and 104 that guides the split light beam from the fiber coupler 102 to a sample 105 (e.g., the eye of a patient) and a reference reflector 106 respectively. For both the sample arm and the reference arm, at the terminating portion of each fiber, there may be a module containing optical elements to collimate or focus or scan the beam. The returned light waves from the sample 105 and the reference reflector 106 are directed back through the same optical path of the sample and reference arms and are combined in fiber coupler 102. A portion of the combined light beam is directed through a section of optical fiber 107 from the fiber coupler 102 to a spectrometer 108. Inside the spectrometer, the light beam is dispersed by a grating 109 and focused onto a detector array 110. The collected data is sent to a processor 111 and the resulting processed data can be displayed on a display 112 or stored in memory for future reference and processing. Although the system of FIG. 1 includes a reflective reference arm, those skilled in the art will understand that a transmissive reference arm could be used in its place.

The interference causes the intensity of the interfered light to vary across the spectrum. The Fourier transform of the interference light reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" *Optics Letters* 36(13): 2390 2011; Y. Nakamura, et al, "High-Speed three dimensional human retinal imaging by line field spectral domain optical coherence tomography" *Optics Express* 15(12):7103 2007; Blazkiewicz et al, "Signal-to-noise ratio study of full-field Fourier-domain optical coherence tomography" *Applied Optics* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system including time domain (TD-OCT), spectral domain (SD-OCT), and/or swept-source (SS-OCT)).

One commercially available SD-OCT system is the Cirrus HD-OCT™ (Carl Zeiss Meditec, Inc. Dublin, Calif.). Several of the measurements provided by this system (e.g., measurements 404, average retinal nerve fiber layer (RNFL) thickness 422, and average cup-to-disc ratio 424 as shown in FIG. 4) could be used in the methods/techniques discussed in the present invention.

Example System for Functional Measurements

Figure 2:
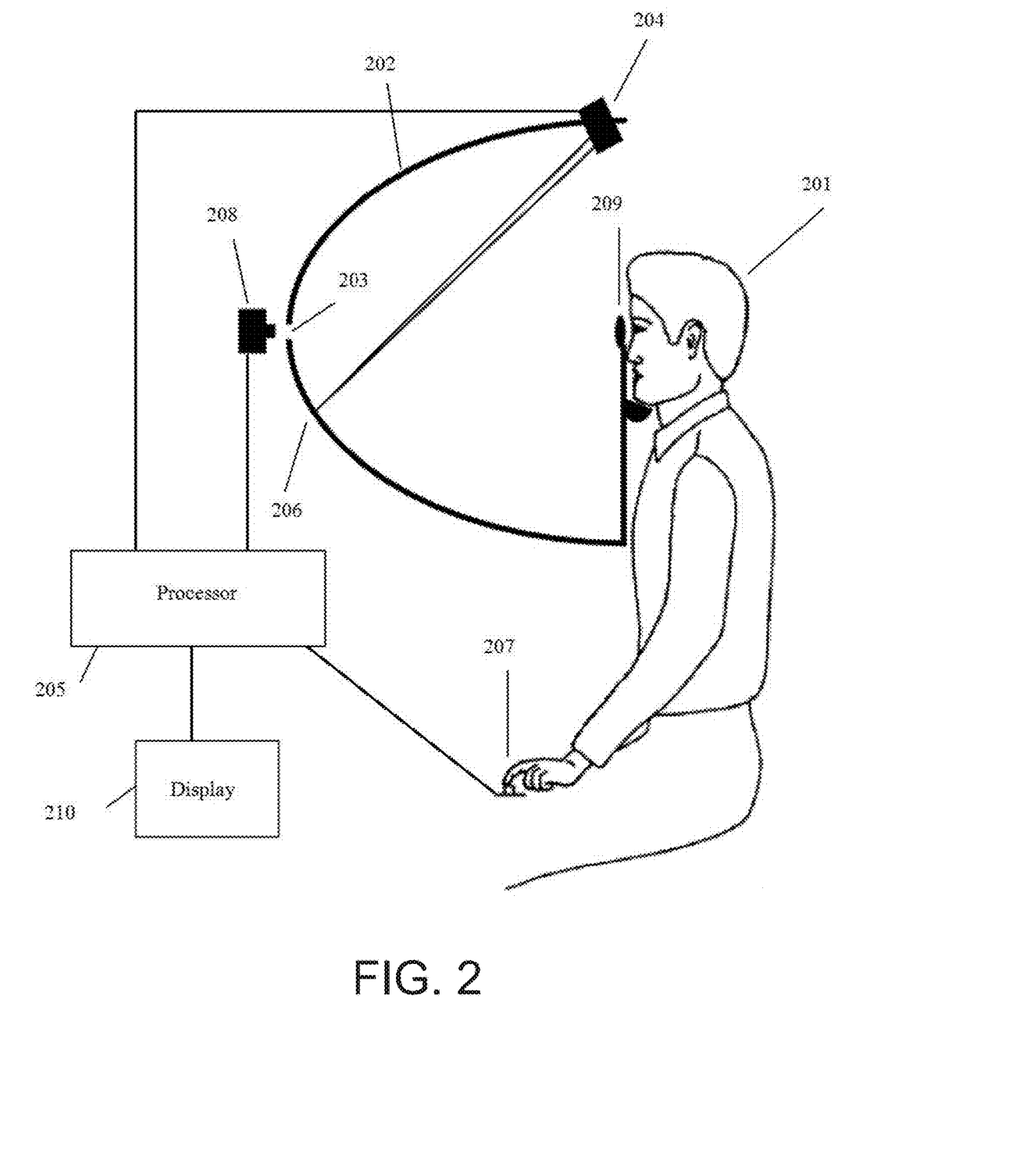
FIG. 2 illustrates another example of an ophthalmic imaging system (specifically, a visual field analyzer) that can be used to collect functional measurements of a patient's eye for use in the present invention.

The Humphrey HFA (Carl Zeiss Meditec, Inc. Dublin, Calif.), is one type of standard automated perimeter that can be used to provide functional measurement data for the present invention. A block diagram of a field analyzer is illustrated in FIG. 2. A patient 201 is shown observing a hemispherical projection screen 202. The patient is instructed to fixate at a point at the center of the hemispherical screen 203. A projector 204 under control of a processor 205 projects a series of spots 206 onto the screen. The patient indicates that the spot 206 of light was seen by depressing button 207. The response is recorded by the processor 205. A camera 208 can be used to monitor the gaze of the patient throughout the test. The images from the gaze camera can optionally be displayed (on display 210) to the clinician for aid in patient alignment or test verification. A trial lens holder 209 is positioned in front of the eye of the patient being tested to correct the refractive error of the patient. The point of projection on the hemispherical projection screen controllably changes to positions spaced apart from the fixation light source. Preferably, the point is varied in intensity as the point moves from position to position on the hemispherical projection screen. By positioning the point to known locations on the hemispherical projection screen and changing the brightness (in a total amount of about four decades), the sensitivity of the patient's retina is measured and mapped. While FIG. 2 shows a projection type visual field tester, the subject invention can be used with other types of visual field testers, including those that generate images through LCD or other displays (see for example, U.S. Pat. No. 8,132,916). A visual field map can be constructed using various analysis algorithms such as the Swedish Interactive threshold algorithm (SITA, see for example U.S. Pat. Nos. 5,461,435; 5,381,195; and 5,598,235).

Figure 4:
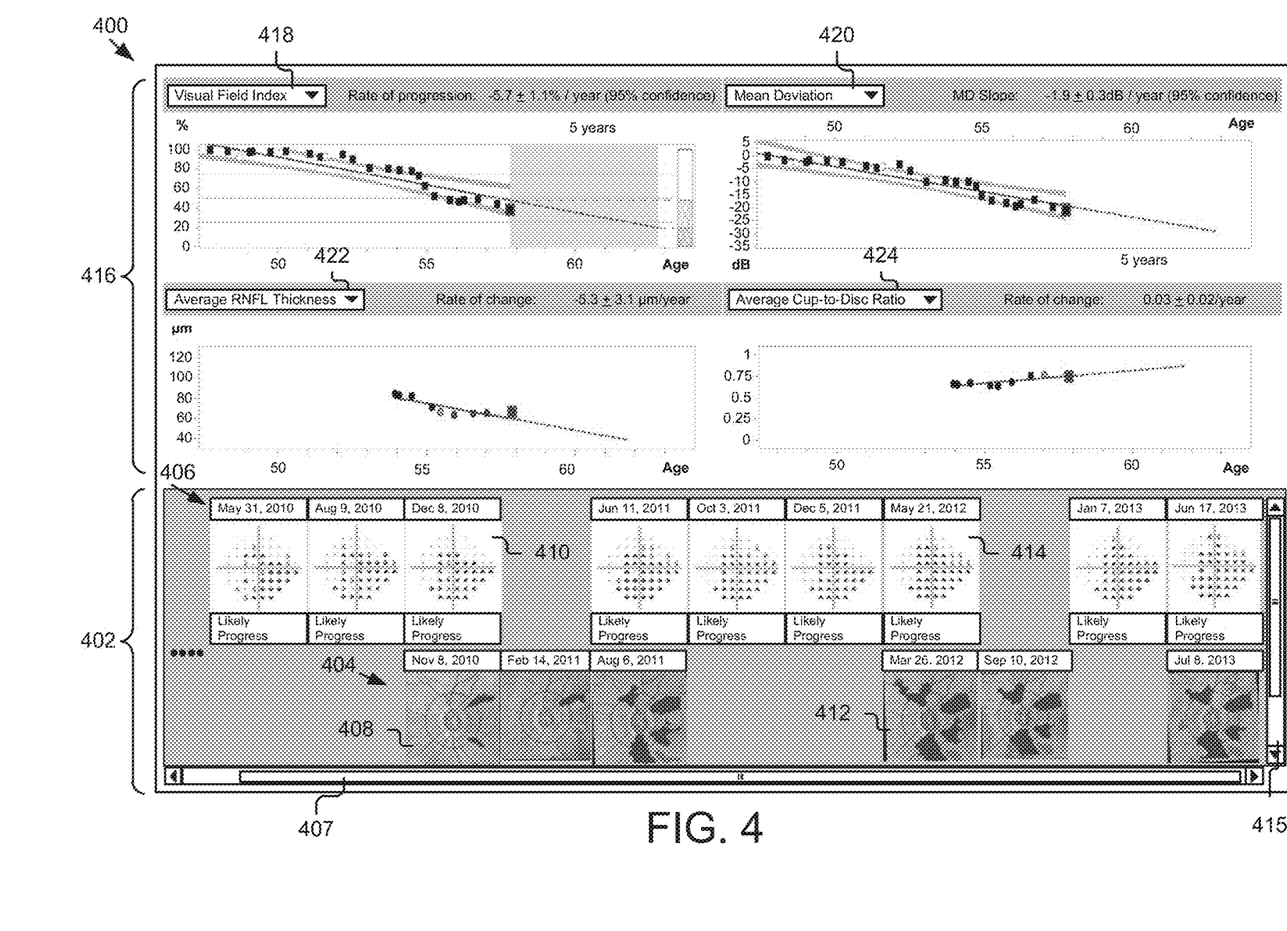
FIG. 4 shows an exemplary graphical user interface of an integrated structural and functional disease progression information of an eye.

The HFA device is capable of providing several different measurements, such as, for example, the pattern deviation maps 406, the visual field index 418, and mean deviation 420 as shown in FIG. 4. The Glaucoma Hemifield Test (GHT) index is available in the standard analysis printout of Standard Automated white-on-white Perimetry (SAP) tests. It is an expert system that classifies SAP tests as within normal limits, borderline or outside normal limits, based on the differences of pattern deviation values between test points in mirror image areas of the upper and lower hemispheres of the visual field.

Combined Structure-Function View for Disease Progression Analysis

Figure 3A:
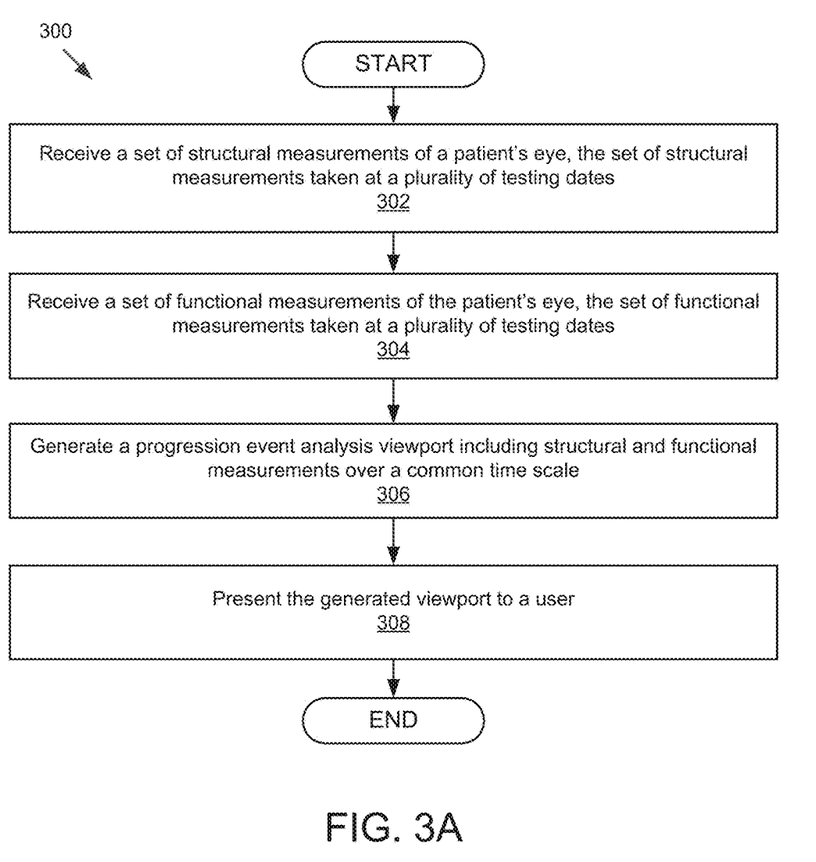
FIG. 3A is a method of displaying progression event analysis information including side by side structural and functional measurements of an eye over a common time scale on the same screen or viewport to a user.
Figure 3B:
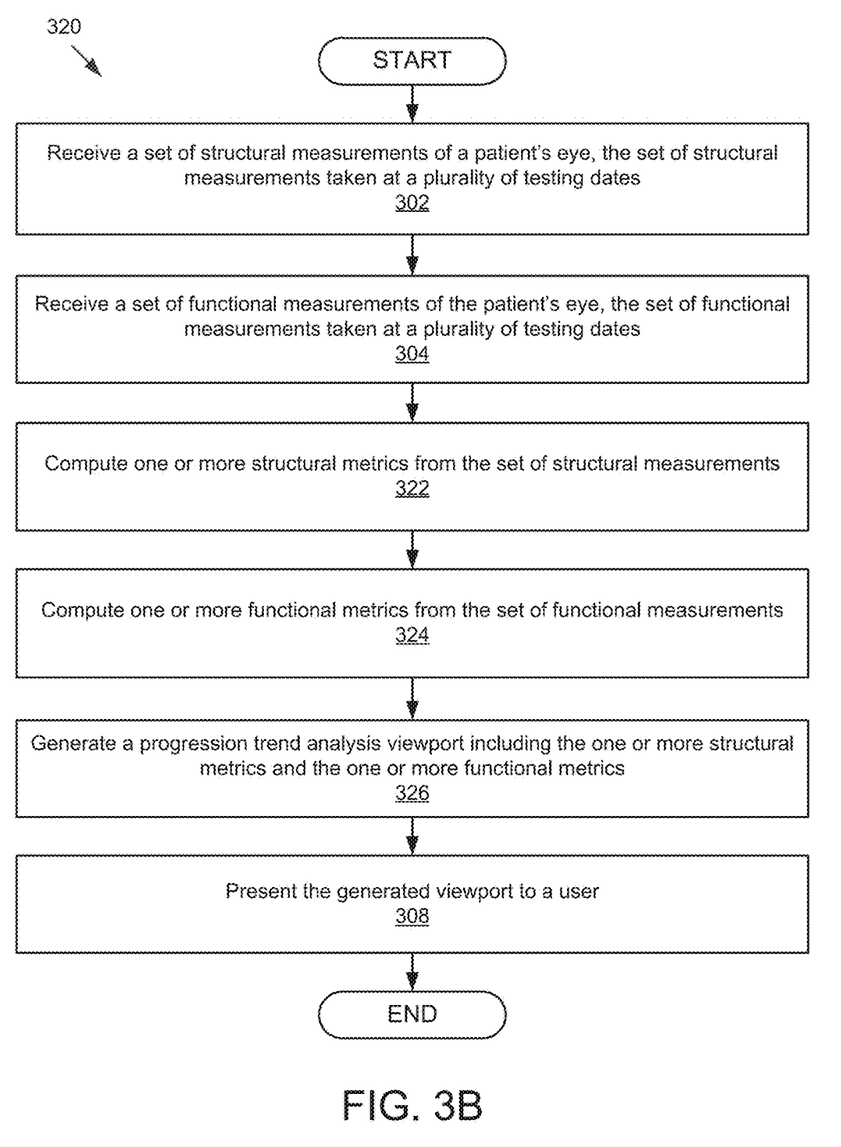
FIG. 3B is a method of displaying progression trend analysis information including one or more structural metrics and one or more functional metrics over a common time axis on the same screen or viewport to a user.
Figure 3C:
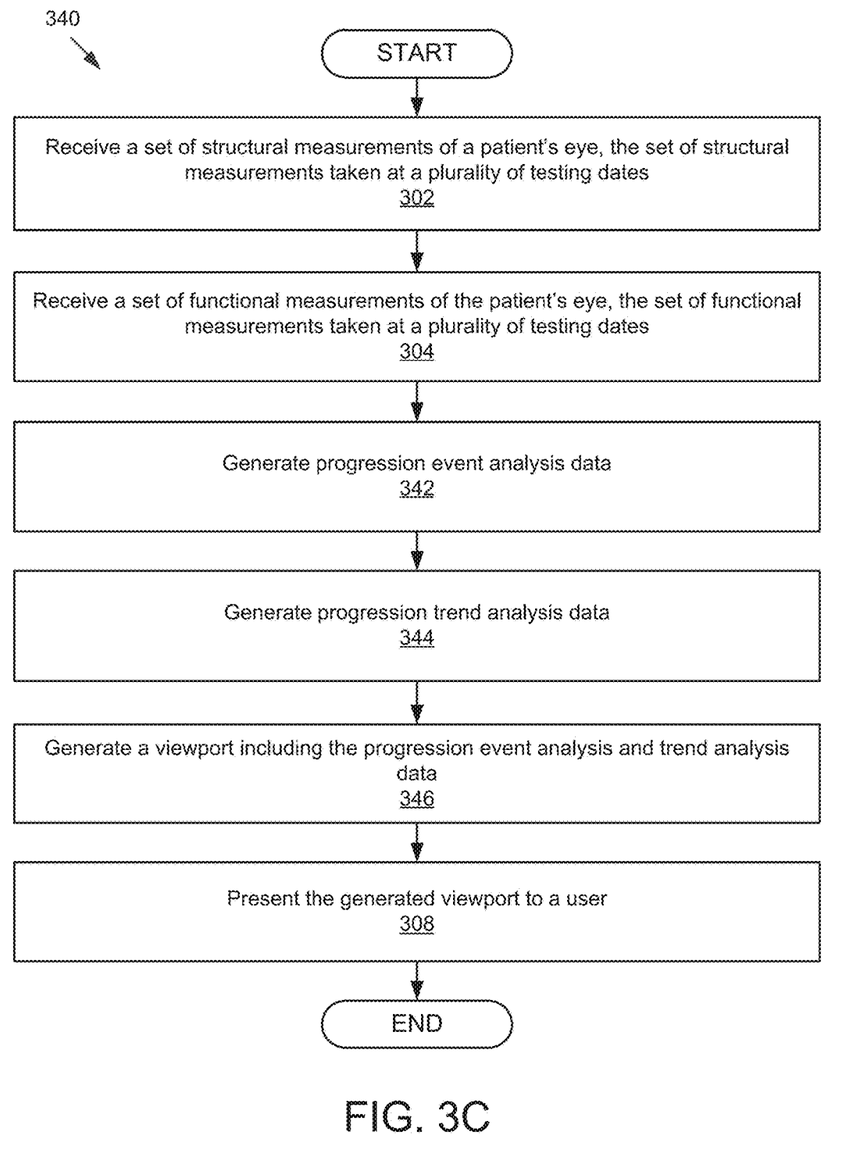
FIG. 3C is a method of displaying progression event analysis as well as progression trend analysis data to a user.

The process of integrating and displaying structural and functional disease progression information of a patient's eye is hereby described in reference to methods 300, 320, and 340 shown in FIGS. 3A-3C, respectively. It should be understood that these methods are not limited to the steps and/or operations referenced in each of these methods and that other steps and/or operations are also possible and are within the scope of the present disclosure. It should also be understood that not every step described herein must be performed.

FIG. 3A is a method 300 of displaying progression event analysis information that includes side by side structural and functional measurements of an eye over a common time scale on the same screen or viewport, as shown for example in the progression event analysis viewport 402 in FIG. 4. In step 302, a set of structural measurements of an eye is received. The set of structural measurements may be OCT measurements of the eye collected using an OCT system such as with the SD-OCT system discussed in reference to FIG. 1. These measurements are taken over a plurality of patient visits or testing dates and indicate disease progression information over time as shown, for example, in the viewport 402. In some embodiments, this set of structural measurements may be stored in a data store (e.g., the data store 514 in FIG. 5) by the OCT system (FIG. 1) and the method 300 may retrieve the measurements from this data store to fulfill the step 302.

In step 304, a set of functional measurements of an eye is received. The set of functional measurements may include visual field test results of the eye collected using a visual field analyzer such as the one discussed in reference to FIG. 2. These functional measurements, similar to structural measurements, are taken over plurality of patient visits or testing dates and indicate disease progression information over time. The testing dates associated with the functional measurements may or may not be the same as the testing dates associated with the structural measurements. In some embodiments, the set of functional measurements may be stored in a data store (such as the data store 514) by the visual field analyzer (FIG. 2) and the method 300 may retrieve the functional measurements from this data store to fulfill the step 304.

Next, in step 306, a progression event analysis viewport is generated that includes both the structural and functional measurements collected over a pre-defined or common time scale (e.g., 3 years). For example, as shown in FIG. 4, the progression event analysis viewport 402 is generated that includes structural measurements 404 and functional measurements 406 of a patient's eye collected during the time period May 31, 2010 to Jul. 8, 2013. Additional structural and/or functional measurements can optionally be viewed by scrolling left (to view past measurements) or right (to view recent measurements) using the horizontal scroll bar 407. For instance, structural and functional measurements taken before May 31, 2010 can be viewed by scrolling to the left using the scroll bar 407 to go backward in time. Furthermore, additional information regarding the displayed structural 406 and functional 404 measurements can optionally be viewed by scrolling downwards using the vertical scroll bar 415. As shown, the structural 404 and functional 406 measurements are arranged side by side and in a chronological order (i.e., oldest to newest) so that they can easily be compared to each other and disease progression based on each can be quickly and efficiently analyzed. Though the two measurements are shown arranged horizontally in the viewport 402, it should be realized that these measurements can be arranged in a vertical side by side representation as well.

As depicted in the viewport 402, the structural and functional measurements that have patient visits or exam/test dates falling within a certain time window (e.g., 90 days) can be placed in close proximity to each other (e.g., on top of each other or next to each other) for comparison purposes. By way of example and with reference to FIG. 4, the structural measurement collected on Nov. 8, 2010 (indicated by reference numeral 408) and the functional measurement collected on Dec. 8, 2010 (indicated by reference numeral 410) are vertically aligned since they were taken within a 1 month difference. By way of another example, the structural measurement collected on Mar. 26, 2012 (indicated by reference numeral 412) and the functional measurement collected on May 21, 2012 (indicated by reference numeral 414) are vertically aligned since their collection dates fall within a 90 day window. It should be understood that those measurements (structural or functional) whose exam/test dates are not matching with another based on the certain time window are still shown in the common time scale, as shown in the viewport 402. In some instances, the progression event analysis viewport 402 discussed herein is generated by an integrated display module 506 of the system 500 (see FIG. 5).

In step 308, the generated viewport is presented to a user. The user may be a doctor, a clinician, or any other person skilled in the field of ophthalmology. The user can view the analysis on any display device, such as for example the display device 510 discussed in reference to FIG. 5.

FIG. 3B is a method 320 of displaying progression trend analysis information including one or more structural and one or more functional metrics over a common time axis on the same screen or viewport to a user, as shown for example in the progression trend analysis viewport 416 in FIG. 4. It should be noted that same reference numerals are used to refer to the steps already discussed above with respect to FIG. 3A and therefore, the description for these steps will not be repeated here.

In step 322, one or more structural metrics are computed from the set of structural measurements received in step 302. For example, for OCT exams, the structural metrics can include average RNFL thickness, inferior RNFL thickness, superior RNFL thickness, cup-to-disc (C/D) ratio, and ganglion cell layer (GCL)+inner plexiform layer (IPL) thickness. In step 324, one or more functional metrics are computed from the set of functional measurements received in step 304. For example, for visual field exams, the functional metrics can include visual field index (VFI), mean deviation (MD), MD for the upper hemifield, and MD for the lower hemifield.

Next, in step 326, a progression trend analysis viewport is generated that includes the one or more structural metrics and the one or more functional metrics. In a default mode, the progression trend analysis viewport includes two structural metrics for OCT results and two functional metrics for visual field results. For example, as shown in FIG. 4, the progression trend analysis viewport 416 includes visual field index 418 and mean deviation 420 as functional metrics and average RNFL thickness 422 and average cup-to disc ratio 424 as structural metrics. It should be noted that the progression trend analysis viewport discussed herein is not limited to this configuration and a variety of other configurations and different metrics are possible and configurable by a user. For instance, the user can select a different structural or functional metric to view by simply clicking on the drop-down menu button associated with each of the metrics 418, 420, 422, and/or 424 and selecting the desired metric. Based on the user selection, the trend analysis viewport 416 will be refreshed to show the results of the selected metric(s) thereon.

As shown in the trend analysis viewport 416, each of the structural metrics (422,424) and the functional metrics (418, 420) are displayed on a common time-axis, which in this case is a range of years of the patient's chronological age. This is advantageous as a user may quickly grasp the temporal relation between each exam (e.g., rate of change or disease progression) by looking at these charts or metrics. The scaling of all charts is such that the same x-axis (time scale) is always used to display both the structural and functional metrics, even if one type of metric is not available over the entire time scale. Zooming and panning of the charts is synchronized, so that the temporal relationship of all the exams is preserved during display. As depicted, the structural and functional metrics are arranged side by side so that they can easily be compared to each other and assessed. Though the metrics are shown arranged horizontally in the viewport 416, it should be realized that these metrics can be arranged in a vertical side-by-side representation as well. In some instances, the progression trend analysis viewport 416 discussed herein is generated by the integrated display module 506 of the system 500 (see FIG. 5).

FIG. 3C is a method 340 of displaying progression event analysis (discussed in reference to FIG. 3A) as well as progression trend analysis data (discussed in reference to FIG. 3B) on the same screen or viewport to a user, as shown for example in the viewport 400 in FIG. 4. It should be noted that same reference numerals are used to refer to the steps already discussed above with respect to FIGS. 3A and 3B, and therefore, the description for these steps will not be repeated here.

Based on a set of structural and functional measurements, progression event analysis data can be generated (step 342) as discussed in reference to FIG. 3A and the progression event analysis viewport 402. Based on the one or more structural and one or more functional metrics respectively derived from the structural and functional measurements, progression trend analysis data can be generated (step 344) as discussed in reference to FIG. 3B and the progression trend analysis viewport 416. In step 346, a viewport is generated that includes both the progression event analysis and the trend analysis data. For example, as shown in FIG. 4, a viewport 400 is generated that is composed of the progression event analysis viewport 402 and the progression trend analysis viewport 416. In a default mode, the progression event analysis data is shown in the lower portion of the viewport 400 and the trend analysis data is shown in the upper portion of the viewport 400. However, it should be noted that the viewport 400 is not limited to this representation and the vice-versa representation is also possible and within the scope of the present disclosure. In some instances, the viewport 400 discussed herein is generated by the integrated display module 506 of the system 500 (see FIG. 5).

The data or information in the viewports 400, 402, and/or 416 can be viewed in three different modes. The first mode is a progression mode that shows disease progression information of a patient's eye over time, for example as shown in the event analysis viewport 402 where a "Triangle Plot" for visual field is displayed above a "Change Map" for OCT exam. The second mode is a deviation mode that shows deviation from age-matched normative values (e.g., pattern deviation for the visual field above a thickness deviation map for OCT exam). The third mode is a raw visualization mode that depicts the measured, non-interpreted values (e.g., greyscale plot for the visual field sensitivities above the thickness map for the OCT exam). In some instances, progression information (for progression mode), deviation from normal information (for deviation mode), and thickness information (for raw visualization mode) of the OCT exams may be from RNFL thickness measurements, from GCL+IPL thickness measurements, or from both.

Example Computer System

Figure 5:
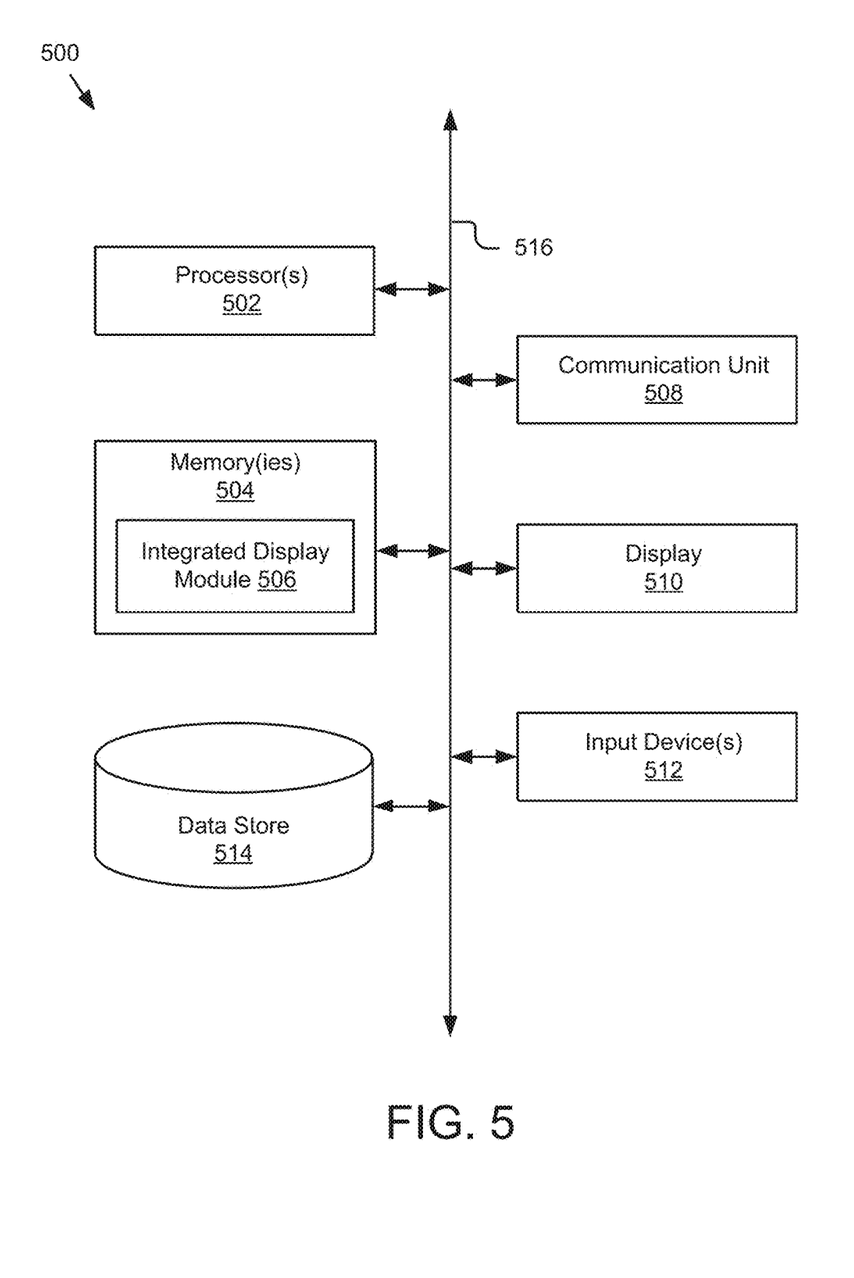
FIG. 5 is a block diagram of a general computer system that may perform the functions discussed in this disclosure according to one aspect of the present invention.

FIG. 5 is a block diagram of a general computer system 500 that may perform the functions discussed in this disclosure according to one aspect of the present invention. The computer system 500, as depicted, may include one or more processors 502, one or more memories 504, a communication unit 508, a display 510, one or more input devices 512, and a data store 514.

The components 502, 504, 508, 510, 512, and 514 are communicatively coupled via a communication or system bus 516. The bus 516 can include a conventional communication bus for transferring data between components of a computing device or between computing devices. It should be understood that the computing system 500 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 502 may execute various hardware and/or software logic, such as software instructions, by performing various input/output, logical, and/or mathematical operations. The processor(s) 502 may have various computing architectures to process data signals including, for example, a complex instruction set computer (CISC) architecture, a reduced instruction set computer (RISC) architecture, and/or architecture implementing a combination of instruction sets. The processor(s) 502 may be physical and/or virtual, and may include a single core or plurality of processing units and/or cores. In some embodiments, the processor(s) 502 may be capable of generating and providing electronic display signals to a display device, such as the display 510, supporting the display of images, capturing and transmitting images, performing complex tasks including various types of feature extraction and sampling, etc. In some embodiments, the processor(s) 502 may be coupled to the memory(ies) 504 via a data/communication bus to access data and instructions therefrom and store data therein. The bus 516 may couple the processor(s) 502 to the other components of the computer system 500, for example, the memory(ies) 504, the communication unit 508, or the data store 514.

The memory(ies) 504 may store instructions and/or data that may be executed by the processor(s) 502. In the depicted embodiment, the memory(ies) 504 stores at least an integrated display module 506, which may include software, code, logic, or routines for performing any and/or all of the techniques described herein. For instance, the integrated display module 506 may perform all or some of the steps/operations depicted in FIGS. 3A-3C and may be capable of generating the viewports 402 and 416, and/or the combined viewport 400 shown in FIG. 4. In some embodiments, the memory(ies) 504 may also be capable of storing other instructions and data including, for example, an operating system, hardware drivers, other software applications, databases, etc. The memory(ies) 504 are coupled to the bus 516 for communication with the processor(s) 502 and other components of the computer system 500. The memory(ies) 504 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 502. A non-transitory computer-usable storage medium may include any and/or all computer-usable storage media. In some embodiments, the memory(ies) 504 may include volatile memory, non-volatile memory, or both. For example, the memory(ies) 504 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system 500 may include one or more computers or processing units at the same or different locations. When at different locations, the computers may be configured to communicate with one another through a wired and/or wireless network communication system, such as the communication unit 508. The communication unit 508 may include network interface devices (I/F) for wired and wireless connectivity. For example, the communication unit 508 may include a CAT-type interface, USB interface, or SD interface, transceivers for sending and receiving signals using Wi-Fi™; Bluetooth®, or cellular communications for wireless communication, etc. The communication unit 508 can link the processor(s) 502 to a computer network that may in turn be coupled to other processing systems.

The display 510 represents any device equipped to display electronic images and data as described herein. The display 510 may be any of a conventional display device, monitor or screen, such as an organic light-emitting diode (OLED) display, a liquid crystal display (LCD). In some embodiments, the display 510 is a touch-screen display capable of receiving input from one or more fingers of a user. For example, the device 510 may be a capacitive touch-screen display capable of detecting and interpreting multiple points of contact with the display surface.

The input device(s) 512 are any devices for inputting data on the computer system 500. In some embodiments, an input device is a touch-screen display capable of receiving input from one or more fingers of the user. The functionality of the input device(s) 512 and the display 510 may be integrated, and a user of the computer system 500 may interact with the system by contacting a surface of the display 510 using one or more fingers. In other embodiments, an input device is a separate peripheral device or combination of devices. For example, the input device(s) 512 may include a keyboard (e.g., a QWERTY keyboard) and a pointing device (e.g., a mouse or touchpad). The input device(s) 512 may also include a microphone, a web camera, or other similar audio or video capture devices.

The data store 514 can be an information source capable of storing and providing access to data. In the depicted embodiment, the data store 514 is coupled for communication with the components 502, 504, 508, 510, and 512 of the computer system 500 via the bus 516, and coupled, via the processor(s) 502, for communication with the integrated display module 506. In some embodiments, the integrated display module 506 is configured to manipulate, i.e., store, query, update, and/or delete, data stored in the data store 514 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. As will be understood by those familiar with the art, the present subject matter may be embodied in other specific forms without departing from the spirit or essential characteristics thereof.

Furthermore, it should be understood that the modules, routines, features, attributes, methodologies and other aspects of the present subject matter can be implemented using hardware, firmware, software, or any combination of the three.

The invention claimed is:

1. A method of displaying combined structural and functional disease progression information of a patient's eye, said method comprising:
   receiving a set of structural measurements of the patient's eye, said set of structural measurements taken at a plurality of testing dates;
   receiving a set of functional measurements of the patient's eye, said set of functional measurements taken at a plurality of testing dates;
   generating a single viewport comprising a side by side display of structural and functional measurements over a common time scale, wherein each of the structural and functional measurements in the generated viewport has a testing date falling within the common time scale; and
   displaying the generated single viewport or storing results of the generated single viewport.

2. The method as recited in claim 1, wherein the structural measurements are optical coherence tomography (OCT) measurements of the patient's eye collected using an OCT system.

3. The method as recited in claim 1, wherein the functional measurements are visual field test results of the patient's eye collected using a visual field analyzer.

4. The method as recited in claim 1, wherein the structural and functional measurements in the generated viewport are arranged in a chronological order of testing dates over the common time scale.

5. The method as recited in claim 4, wherein a structural measurement and a functional measurement that have testing dates falling within a certain time duration are placed in close proximity to each other.

6. The method as recited in claim 1, wherein the side by side display is horizontal.

7. The method as recited in claim 1, wherein the generated viewport further comprises a second side by side display of one or more metrics from the structural measurements and one or more metrics from the functional measurements.

8. The method as recited in claim 7, wherein the one or more metrics from the structural measurements are chosen from a group consisting of a visual field index (VFI), a mean deviation (MD), a MD for the upper hemifield, and a MD for the lower hemifield.

9. The method as recited in claim 7, wherein the one or more metrics from the functional measurements are chosen from a group consisting of average retinal nerve fiber layer (RNFL) thickness, inferior RNFL thickness, superior RNFL thickness, cup-to-disc (C/D) ratio, and ganglion cell layer (GCL) plus inner plexiform layer (IPL) thickness.

10. The method as recited in claim 1, wherein the disease is glaucoma.

11. The method as recited in claim 1 further comprising:
    printing the results of the generated single viewport as a report; and
    providing the report to a doctor or clinician for further analysis thereof.

12. A method of displaying combined structural and functional disease progression information of a patient's eye, said method comprising:
    receiving a set of structural measurements of the patient's eye, said set of structural measurements taken at a plurality of testing dates;
    receiving a set of functional measurements of the patient's eye, said set of functional measurements taken at a plurality of testing dates;
    computing one or more structural metrics from the set of structural measurements;
    computing one or more functional metrics from the set of functional measurements;
    generating a single viewport comprising a side by side display of the one or more structural metrics and the one or more functional metrics, wherein the one or more structural metrics and the one or more functional metrics are each displayed on a common time axis; and
    displaying the generated single viewport or storing results of the generated single viewport.

13. The method as recited in claim 12, wherein the structural measurements are optical coherence tomography (OCT) measurements of the patient's eye collected using an OCT system.

14. The method as recited in claim 12, wherein the functional measurements are visual field test results of the patient's eye collected using a visual field analyzer.

15. The method as recited in claim 12, wherein the one or more structural metrics and the one or more functional metrics are user selectable.

16. The method as recited in claim 15, wherein the one or more structural metrics are selected from a group consisting of a visual field index (VFI), a mean deviation (MD), a MD for the upper hemifield, and a MD for the lower hemifield.

17. The method as recited in claim 15, wherein the one or more functional metrics are selected from a group consisting of average retinal nerve fiber layer (RNFL) thickness, inferior RNFL thickness, superior RNFL thickness, cup-to-disc (C/D) ratio, and ganglion cell layer (GCL) plus inner plexiform layer (IPL) thickness.

18. The method as recited in claim 12, wherein the generated viewport further comprises a second side by side display of structural and functional measurements over a common time scale, wherein each of the structural and functional measurements in the second side by side display has a testing date falling within the common time scale.

19. The method as recited in claim 18, wherein the structural and functional measurements are arranged in a chronological order of testing dates over the common time scale.

20. The method as recited in claim 19, wherein a structural measurement and a functional measurement that have testing dates falling within a certain time duration are placed in close proximity to each other.

21. A method of displaying combined structural and functional disease progression information of a patient's eye, said method comprising:
    receiving a set of structural measurements of the patient's eye, said set of structural measurements taken at a plurality of testing dates;
    receiving a set of functional measurements of the patient's eye, said set of functional measurements taken at a plurality of testing dates;
    computing one or more structural metrics from the set of structural measurements;
    computing one or more functional metrics from the set of functional measurements;
    generating a single viewport comprising 1) a first side by side display of the one or more structural metrics and the one or more functional metrics, wherein the one or more structural metrics and the one or more functional metrics are each displayed on a common time axis, and 2) a second side by side display of structural and functional measurements over a common time scale, wherein each of the structural and functional measurements in the second side by side display has a testing date falling within the common time scale; and displaying the generated single viewport or storing results of the generated single viewport.

22. The method as recited in claim 21, wherein the structural measurements are optical coherence tomography (OCT) measurements of the patient's eye collected using an OCT system.

23. The method as recited in claim 21, wherein the functional measurements are visual field test results of the patient's eye collected using a visual field analyzer.

24. The method as recited in claim 21, wherein the one or more structural metrics are selected from a group consisting of a visual field index (VFI), a mean deviation (MD), a MD for the upper hemifield, and a MD for the lower hemifield.

25. The method as recited in claim 21, wherein the one or more functional metrics are selected from a group consisting of average retinal nerve fiber layer (RNFL) thickness, inferior RNFL thickness, superior RNFL thickness, cup-to-disc (C/D) ratio, and ganglion cell layer (GCL) plus inner plexiform layer (IPL) thickness.

26. The method as recited in claim 21, wherein the structural and functional measurements in the second side by side display are arranged in a chronological order of testing dates over the common time scale.

27. The method as recited in claim 26, wherein a structural measurement and a functional measurement that have testing dates falling within a certain time duration are placed in close proximity to each other.

28. The method as recited in claim 21, wherein the first and the second side by side displays are horizontal.

29. The method as recited in claim 21, wherein data in the generated viewport is viewable in three different modes, said three different modes including 1) a progression mode that shows disease progression information over time, 2) a deviation mode that shows deviation from age relating normative values, and 3) a raw visualization mode that shows thickness measurements or information in a thickness map.

30. The method as recited in claim 21, wherein the disease is glaucoma.

\* \* \* \* \*

UNITED STATES PATENT AND TRADEMARK OFFICE
CERTIFICATE OF CORRECTION

PATENT NO. : 9,968,251 B2
APPLICATION NO. : 15/281497
DATED : May 15, 2018
INVENTOR(S) : Tobias Kurzke et al.

It is certified that error appears in the above-identified patent and that said Letters Patent is hereby corrected as shown below:

In the Specification

In Column 4, Line 60, delete "OCT))." and insert -- OCT). --, therefor.

Signed and Sealed this
Eleventh Day of December, 2018

Andrei Iancu
*Director of the United States Patent and Trademark Office*